United States Patent
Chiu et al.

(10) Patent No.: US 10,485,696 B2
(45) Date of Patent: Nov. 26, 2019

(54) THERMAL THERAPY DEVICE WITH INTERCHANGEABLE HOT AND COLD WATER CIRCULATION AND AIR PRESSURE CONTROL

(71) Applicants: Gary Chiu, Plano, TX (US); Li Wang, Plano, TX (US)

(72) Inventors: Gary Chiu, Plano, TX (US); Li Wang, Plano, TX (US)

( * ) Notice: Subject to any disclaimer, the term of this patent is extended or adjusted under 35 U.S.C. 154(b) by 414 days.

(21) Appl. No.: 15/378,287

(22) Filed: Dec. 14, 2016

(65) Prior Publication Data

US 2018/0161199 A1    Jun. 14, 2018

(51) Int. Cl.
*A61F 7/00* (2006.01)
*A61F 7/08* (2006.01)

(52) U.S. Cl.
CPC .......... *A61F 7/0085* (2013.01); *A61F 7/0097* (2013.01); *A61F 7/08* (2013.01); *A61F 2007/0086* (2013.01); *A61F 2007/0091* (2013.01)

(58) Field of Classification Search
CPC combination set(s) only.
See application file for complete search history.

(56) References Cited

U.S. PATENT DOCUMENTS

| | | | |
|---|---|---|---|
| 2016/0022477 A1* | 1/2016 | Schaefer | A61F 7/0085 607/104 |
| 2016/0022478 A1* | 1/2016 | Schaefer | A61F 7/0085 607/104 |

* cited by examiner

*Primary Examiner* — Joseph A Stoklosa
*Assistant Examiner* — Adam J Avigan
(74) *Attorney, Agent, or Firm* — Sinorica, LLC (57) ABSTRACT

A thermal therapy device can be operated for both cold and hot water circulation by using a self-priming pump and four solenoid valves with the open/closed states selectively controlled by an MCU to pump chilled water or cold water from two different water containers to sequentially circulate through two different water paths to a water bladder for cold therapy treatment or hot therapy treatment. During the hot therapy treatment, a water heater is used to heat the cold water until a configured temperature is reached. A pneumatic pump is also employed to carry out an air pressure control mode to pump air into an air bladder securely attached on the water bladder to put pressure on the water bladder for a pressurized treatment. Water retained in the water bladder can also be evacuated and returned to the two different water containers to avoid moss generation and stinky odor.

12 Claims, 7 Drawing Sheets

THERMAL THERAPY DEVICE WITH INTERCHANGEABLE HOT AND COLD WATER CIRCULATION AND AIR PRESSURE CONTROL

BACKGROUND OF THE INVENTION

1. Field of the Invention

The present invention relates to a thermal therapy device and, more particularly, to a thermal therapy device with combined functions of heating/cooling water inside the thermal therapy device and applying air compression for the purpose of relieving muscle pain and soreness and improving blood circulation.

2. Description of the Related Art

Cold therapy, cryo/cuff cold therapy and fomentation therapy are common thermal treatments in the field of rehabilitation. Although the foregoing therapies can be provided through various types of therapy equipment, most conventional therapy equipment is only provided for one type of therapy instead of being treated as comprehensive therapy equipment for all types of therapies. Besides, there are at least the following issues occurring upon the use of conventional therapy equipment.

As far as cold therapy and cryo/cuff cold therapy are concerned, there are several following ways available in the current market.

1. Directly add ice cubes into a simple ice pack. As the temperature of the added ice cubes is close to zero (° C.), the ice pack is not good for direct or indirect contact to the skin for a long time, which easily causes frostbite. Also because the ice cubes may have sharp edges and corners, the ice pack causes discomfort in use.

2. Pour large amount of ice cubes and water into a pail and put the body portion to be treated into the pail, which is also prone to frostbite.

3. Use a plastic or metal container for storage of water and ice cubes and install a water pump for circulation of ice water. If the ice water is continuously circulated without intermittent pause in operation, there is a likelihood that users may get frostbite and it consumes more electricity. Such an approach fails to offer users with different functions to choose and fails to allow users to have the optimal treatment effect through the most effective way depending on the need of therapy.

As far as fomentation therapy is concerned, there are several following ways available in the current market.

1. Hand warmers generate heat through chemical reaction to achieve the effect of fomentation. Despite an easy solution, chemical substances contained in the hand warmers may cause environmental pollution and danger due to inappropriate usage and may be inadvertently swallowed by infants and children. Another issue of hand warmers is that temperature fails to be maintained constantly throughout the fomentation because chemical substances are gradually used up, causing reduced heating temperature or reduced fomentation effect.

2. Fill conventional cold therapy equipment with hot water for fomentation. Such an approach is ineffective in water temperature control and easily burns users' skin. As such conventional cold therapy equipment is not capable of self-heating, no obvious treatment effect arises from fast temperature drop.

3. Use stationary metal container and heater to heat up cold water in the container, and use a water pump to pump heated water to a water bag for fomentation. The water pump in such an approach is damage-prone because of the need for long heating time and pumping of the heated water.

Additionally, conventional cold therapy equipment fails to evacuate water retained in the water bag after use and the water kept in the water bag emits stinky odor and grows moss, potentially causing malfunction of the equipment.

SUMMARY OF THE INVENTION

An objective of the present invention is to provide a thermal therapy device with interchangeable hot and cold water circulation and air pressure control capable of providing both cold therapy treatment and hot therapy treatment with pressure applied and evacuating water retained in the water bladder.

To achieve the foregoing objective, the thermal therapy device includes an enclosure, an ice and water containing unit, a water switching and circulation unit, a water heating unit, a water temperature sensing unit, a therapy bladder assembly, an air supply and pressure monitoring unit, and a microcontroller unit (MCU).

The enclosure has a control panel mounted thereon for configuring a water circulation mode, a water temperature threshold, an air pressure control mode, and an air pressure threshold.

The ice and water containing unit has a mixed ice and water container and a cold water container.

The mixed ice and water container is detachably mounted on the enclosure, is filled with ice and water, provides chilled water to be circulated for cold therapy treatment, and has a water inlet and a water outlet.

The cold water container is detachably mounted on the enclosure, is filled with water to be circulated for hot therapy treatment, and has a water inlet and a water outlet.

The water switching and circulation unit is securely mounted inside the enclosure and has a self-priming pump and a first solenoid valve, a second solenoid valve, a third solenoid valve and a fourth solenoid valve.

The self-priming pump drives to circulate water or air entering therein.

The first solenoid valve, the second solenoid valve, the third solenoid valve and the fourth solenoid valve are normally closed. The first solenoid valve is connected to the water inlet of the mixed ice and water container through a water conduit, the second solenoid valve is connected to the water outlet of the mixed ice and water container and the self-priming pump through water conduits, the third solenoid valve is connected to the water outlet of the cold water container and the self-priming pump through water conduits, and the fourth solenoid valve is connected to the water inlet of the cold water container through a water conduit.

The water heating unit is securely mounted inside the enclosure, is connected with the self-priming pump through a water conduit, and heats water supplied from the self-priming pump.

The water temperature sensing unit is securely mounted inside the enclosure, is connected with the water heating unit through a water conduit, and senses temperature of water passing through the water temperature sensing unit.

The therapy bladder assembly is connected with the first solenoid valve and the fourth solenoid valve through water conduits, and has a water bladder and an air bladder.

The water bladder is adapted to be placed on a body portion requiring a therapy treatment under the water circulation mode and has an inlet and an outlet.

The air bladder is securely attached to a periphery of the water bladder.

The air supply and pressure monitoring unit is securely mounted inside the enclosure, is connected to air bladder, supplies air to the air bladder to put pressure on the water bladder under the air pressure control mode, and senses an air temperature in the air bladder.

The MCU is securely mounted inside the control panel and is electrically connected to the self-priming pump, the first solenoid valve, the second solenoid valve, the third solenoid valve, the fourth solenoid valve, the water heating unit, the water temperature sensing unit, and the air supply and pressure monitoring unit. Under the water circulation mode, the MCU turns on the self-priming pump, selectively switches a part of the first solenoid valve, the second solenoid valve, the third solenoid valve and the fourth solenoid valve to be open, and selectively turns on the water heater to continuously heat circulated water or turns off the water heater throughout the water circulation mode to maintain a water temperature of the circulated water sensed by the water temperature sensing unit at the water temperature threshold. Under the air pressure control mode, the MCU turns on the air supply and pressure monitoring unit to inflate or deflate the air bladder to maintain an air pressure of the air bladder sensed by the air supply and pressure monitoring unit at the air pressure threshold.

Preferably, the control panel serves for further configuring a water return mode, and under the water return mode, the water conduits connected with the water outlets of the mixed ice and water container and the cold water container are manually unplugged from the outlet, the MCU turns on the self-priming pump and switches a first solenoid valve, a second solenoid valve, a third solenoid valve and a fourth solenoid valve to be open, air sucked in by the self-priming pump through the water conduits unplugged from the water outlet of the mixed ice and water container sequentially passes through the second solenoid valve, the first T tube, the self-priming pump, the water heater, the water temperature sensing unit, and the water inlet of the three-way connector to enter the water bladder, and water retained in the water bladder is partially pushed by the air to sequentially circulate through the water outlet of the three-way connector and the second T tube and return to the mixed ice and water container through the first solenoid valve and to the cold water container through the fourth solenoid valve, air sucked in by the self-priming pump through the water conduit unplugged from the water outlet of the cold water container sequentially passes through the third solenoid valve, the first T tube, the self-priming pump, the water heater, the water temperature sensing unit, and the water inlet of the three-way connector to enter the water bladder, and the water retained in the water bladder is partially pushed by the air to sequentially circulate through the water outlet of the three-way connector and the second T tube and returns to the mixed ice and water container through the first solenoid valve and to the cold water container through the fourth solenoid valve.

As can be seen from the foregoing description, the thermal therapy device employs the self-priming pump and four solenoid valves to establish different water circulation paths for chilled water and cold water by switching the open/closed state of the solenoid valves and turning on the self-priming pump. In the case of hot therapy treatment, the water heater is turned on to heat up the cold water passing through. As such, the hot therapy treatment and the cold therapy treatment can be interchangeably provided and coexist in the thermal therapy device. Also because of the air pressure control mode, the air bladder mounted on the water bladder can be inflated to put an adjustable pressure on the water bladder for the water bladder to be wrapped around a body portion requiring a thermal treatment with a desired tightness. As the water return mode allows users to evacuate water retained in the water bladder and return the evacuated water to the mixed ice and water container and the cold water container, operational hygiene of the thermal therapy device can be ensured as a result of no moss generation and stinky odor arising from water retained in the water bladder.

Other objectives, advantages and novel features of the invention will become more apparent from the following detailed description when taken in conjunction with the accompanying drawings.

DETAILED DESCRIPTION OF THE INVENTION

Figure 1:
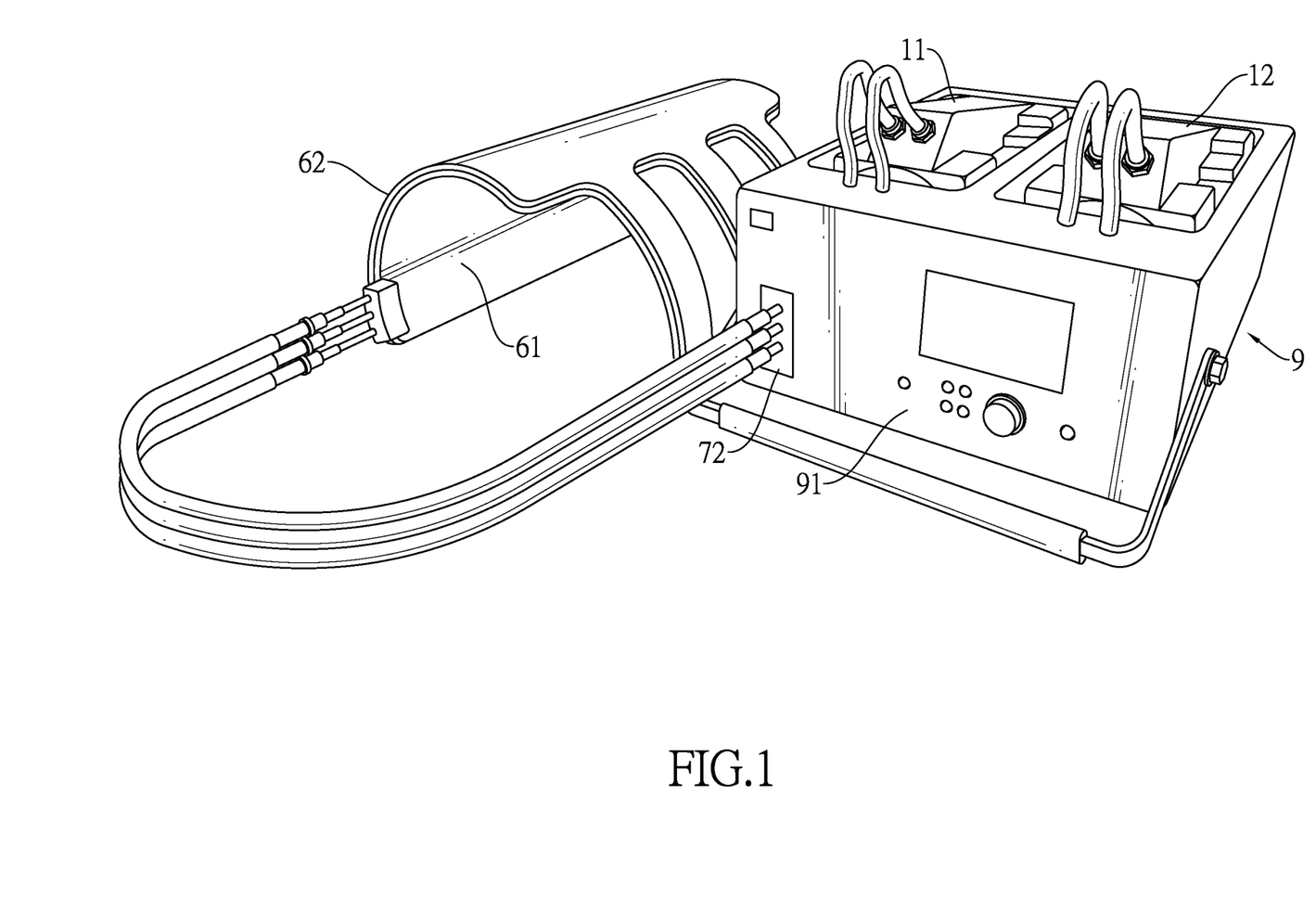
FIG. 1 is a perspective view of a thermal therapy device with interchangeable hot and cold water circulation and air pressure control in accordance with the present invention.
Figure 2:
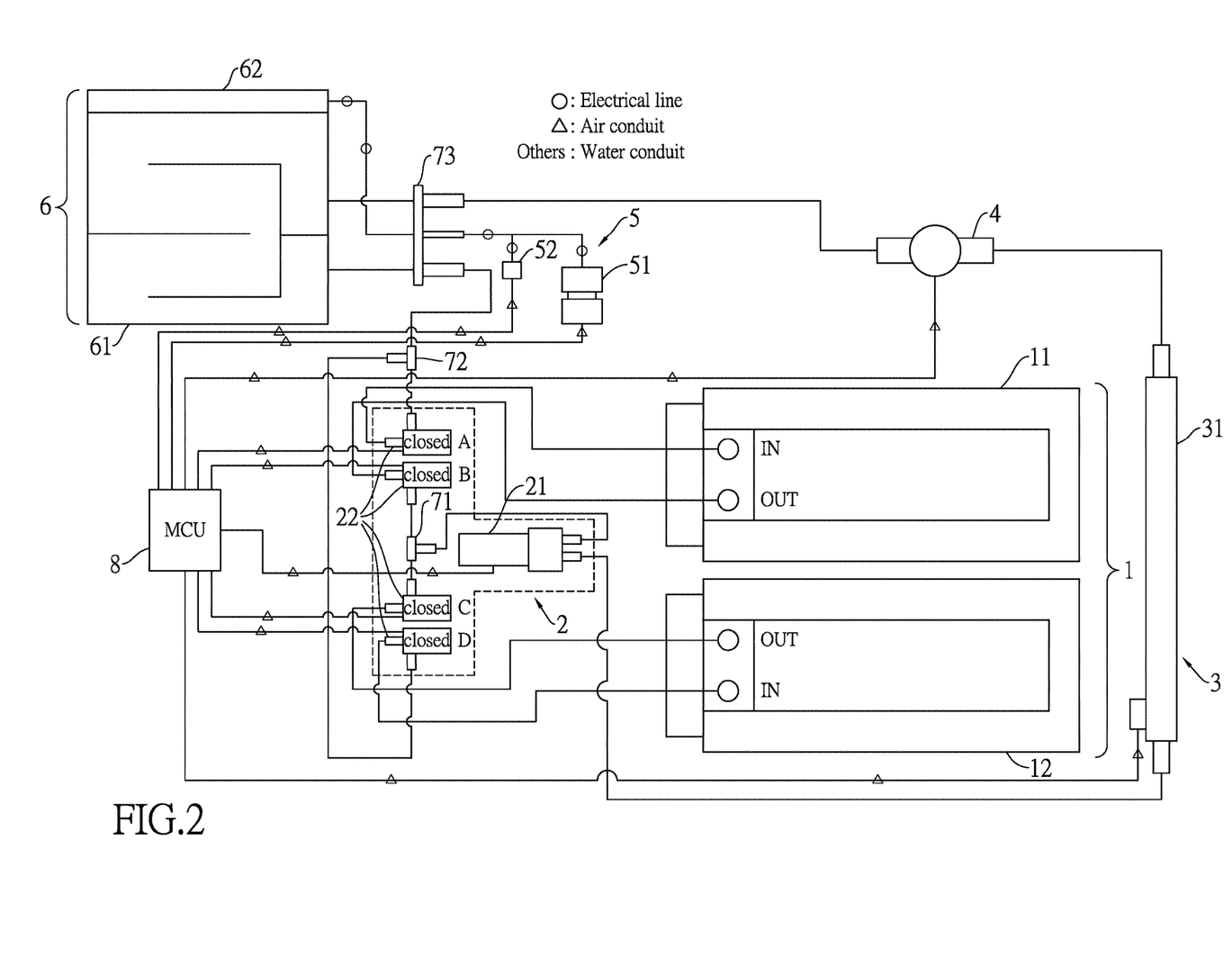
FIG. 2 is a schematic diagram showing the thermal therapy device in FIG. 1.

With reference to FIGS. 1 and 2, a thermal therapy device with interchangeable hot and cold water circulation and air pressure control in accordance with the present invention includes an enclosure 9, a water and air conduit connection unit, an ice and water containing unit 1, a water switching and circulation unit 2, a water heating unit 3, a water temperature sensing unit 4, an air supply and pressure monitoring unit 5, a therapy bladder assembly 6, and a micro-controller unit (MCU) 8.

The enclosure 9 has a control panel 91 mounted thereon for configuring a water circulation mode, a water temperature threshold for the hot water circulation mode, an air pressure control mode, and an air pressure threshold for the air pressure control mode.

The water and air conduit connection unit is securely mounted inside the enclosure 9 and has a first T tube 71, a second T tube 72 and a three-way connector 73. Each of the first T tube 71 and the second T tube 72 has three ports for circulated water to pass through. The three-way connector 73 has a water inlet, a water outlet and one air passage. The water inlet and the water outlet allow circulated water to enter and exit from the three-way connector 73 and the air passage allows air to pass through.

The ice and water containing unit 1 has a mixed ice and water container 11 and a cold water container 12. The mixed ice and water container 11 is detachably mounted on the enclosure 9, is filled with mixed ice and water therein, and has a water inlet and a water outlet for circulated water to enter and exit from the mixed ice and water container 11. The cold water container 12 is detachably mounted on the enclosure 9 and has a water inlet and a water outlet for circulated water to enter and exit from the cold water container 12.

The water switching and circulation unit 2 is securely mounted inside the enclosure 9 and has a self-priming pump 21 and four solenoid valves 22. The self-priming pump 21 has an inlet and an outlet. The inlet of the self-priming pump 21 is connected to one of the three ports of the first T tube 71 through a water conduit. The four solenoid valves 22 represented by letters A, B, C and D are normally closed and each solenoid valve 22 has two ports. One port of the solenoid valve represented by A is connected to the water inlet of the mixed ice and water container 11 through a water conduit, and the other port of the solenoid valve represented by A is connected to one of the three ports of the second T tube 72 through a water conduit. One port of the solenoid valve represented by B is connected to the water outlet of the mixed ice and water container 11 through a water conduit, and the other port of the solenoid valve represented by B is connected to another port of the first T tube 71 through a water conduit. One port of the solenoid valve represented by C is connected to a remaining port of the first T tube 71 through a water conduit, and the other port of the solenoid valve represented by C is connected to the water outlet of the cold water container 12 through a water conduit. One port of the solenoid valve represented by D is connected to the water inlet of the cold water container 12, and the other port of the solenoid valve represented by D is connected to another port of the second T tube 72.

The water heating unit 3 is securely mounted inside the enclosure 9 and has a water heater 31 and an over-heat relay 32. The water heater 31 is mounted on a water conduit connected between the outlet of the self-priming pump 21 and the water temperature sensing unit 4 to heat water passing through the water conduit on which the water heater 31 is mounted. The over-heat relay 32 is connected to the water heater 31 to automatically switch off the water heater 31 when water temperature sensed is equal to or greater than the water temperature threshold.

The water temperature sensing unit 4 is securely mounted inside the enclosure 9 and is connected between the water heater 31 and the water inlet of the three-way connector 73 through water conduits to sense temperature of water passing through the water temperature sensing unit 4.

The air supply and pressure monitoring unit 5 is securely mounted inside the enclosure 9 and has a pneumatic pump 51 and a pressure sensor 52. The pneumatic pump 51 is connected to the air passage of the three-way connector 73 through an air conduit to supply air. The pressure sensor 52 is connected between the pneumatic pump 51 and the three-way connector 73 through another air conduit to sense the pressure of air pumped by the pneumatic pump 51.

The therapy bladder assembly 6 is connected with the enclosure 9 through air and water conduits and has a water bladder 61 and an air bladder 62. The water bladder 61 is placed on a body portion requiring a therapy treatment and has an inlet and an outlet. The inlet of the water bladder 61 is connected to the water inlet of the three-way connector 73 for circulated water to enter the water bladder 61. The outlet of the water bladder 61 is connected to the water outlet of the three-way connector 73 for circulated water to exit from the water bladder 61. The air bladder 62 is securely attached to a periphery of the water bladder 61 and is operated under an inflate mode and an inflate and deflate mode. During the inflate mode, the air bladder 62 is inflated to and maintained at the air pressure threshold according to the air pressure measured by the pressure sensor 52. During the inflate and deflate mode, the air bladder 62 is inflated to the air pressure threshold for one minute, is deflated to 5 mmHg for 30 seconds, and is inflated back to the air pressure threshold, and the air bladder 62 is inflated and deflated according to this cycle. When the air pressure inside the air bladder 62 increases, the air pressure of the air bladder 62 compresses against the water bladder 61 to put pressure on the body portion requiring a therapy treatment. When the air pressure inside the air bladder 62 decreases, the portion requiring therapy treatment is relieved from a compressed state.

The MCU 8 is securely mounted inside the control panel 91 and is electrically connected to the self-priming pump 21, the four solenoid valves 22, the water heater 31, the over-heat relay 32, the water temperature sensing unit 4, the pneumatic pump 51 and the pressure sensor 52. For the water circulation mode, the MCU 8 turns on the self-priming pump 21, selectively switches the solenoid valves 22 to be open, and selectively turns on the water heater 31 to continuously heat circulated water or turns off the water heater 31 throughout the water circulation mode to maintain water temperature of the circulated water sensed by the water temperature sensing unit 4 at the water temperature threshold. For the air pressure control mode, the MCU 8 turns on the pneumatic pump 51 to inflate or deflate the air bladder 62 to maintain air pressure of the air bladder sensed by the pressure sensor 52 at the air pressure threshold.

Figure 3:
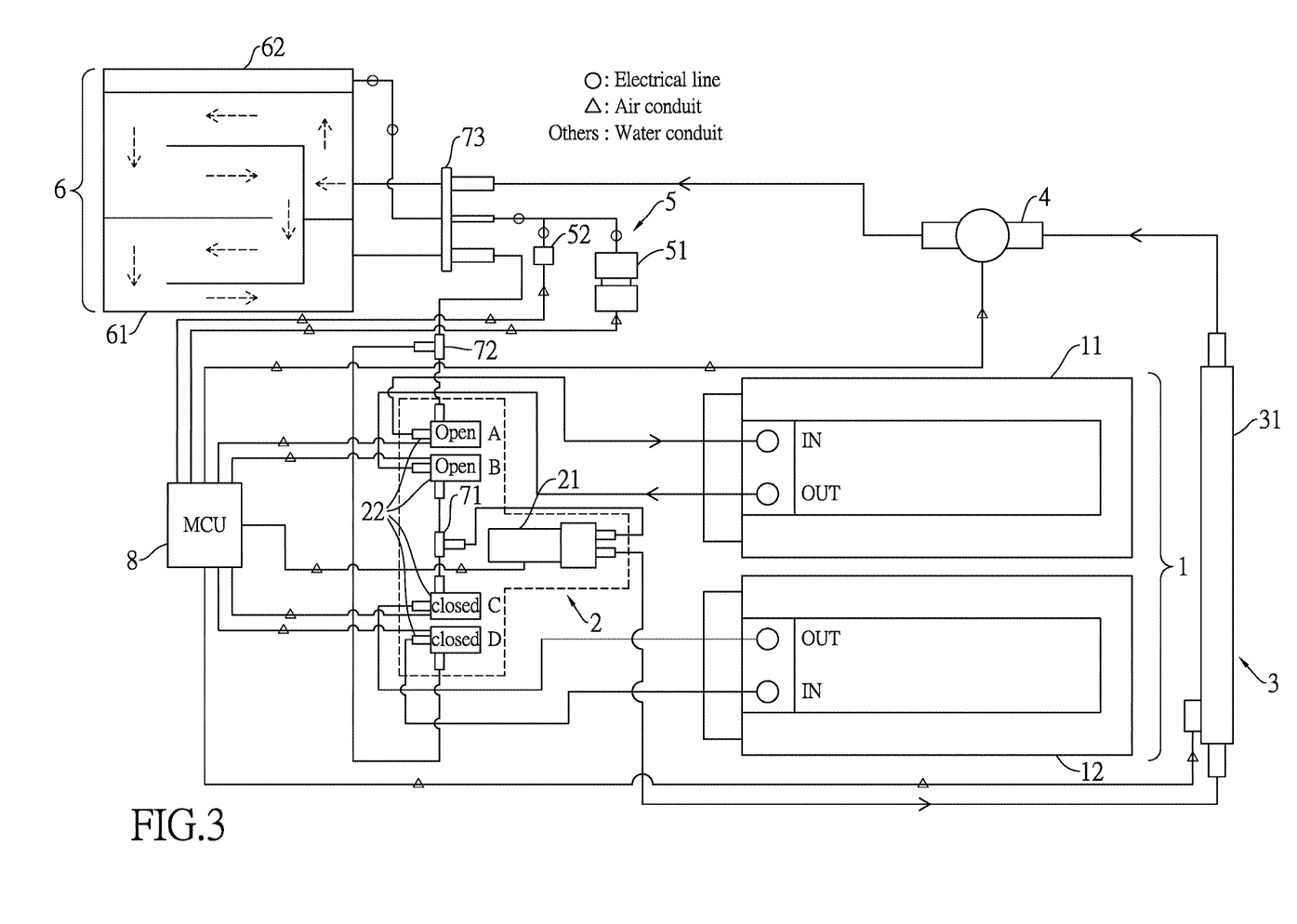
FIG. 3 is an operational schematic diagram showing the thermal therapy device in FIG. 2 under cold water circulation mode.

As far as water circulation is concerned, the foregoing water circulation mode may be a cold water circulation mode and a hot water circulation mode. With reference to FIG. 3, when the thermal therapy device is operated under the cold water circulation mode, the MCU 8 turns on the self-priming pump 21 and switches the two solenoid valves represented by A and B to be open and switches the other two solenoid valves represented by C and D to be closed, water in the mixed ice and water container 11 is pumped by the self-priming pump 21 to sequentially circulate through the solenoid valve B, the first T tube 71, the self-priming pump 21, the water heater 31, the water temperature sensing unit 4, the water inlet of the three-way connector 73, the water bladder 61, the water outlet of the three-way connector 73, the second T tube 72, and the solenoid valve A, and returns to the mixed ice and water container 11. During the cold water circulation mode, the water heater 31 is not turned on and the chilling effect of the circulated water in the water bladder 61 provides cold therapy treatment when the water bladder 61 is placed on a body portion to be treated.

Figure 4:
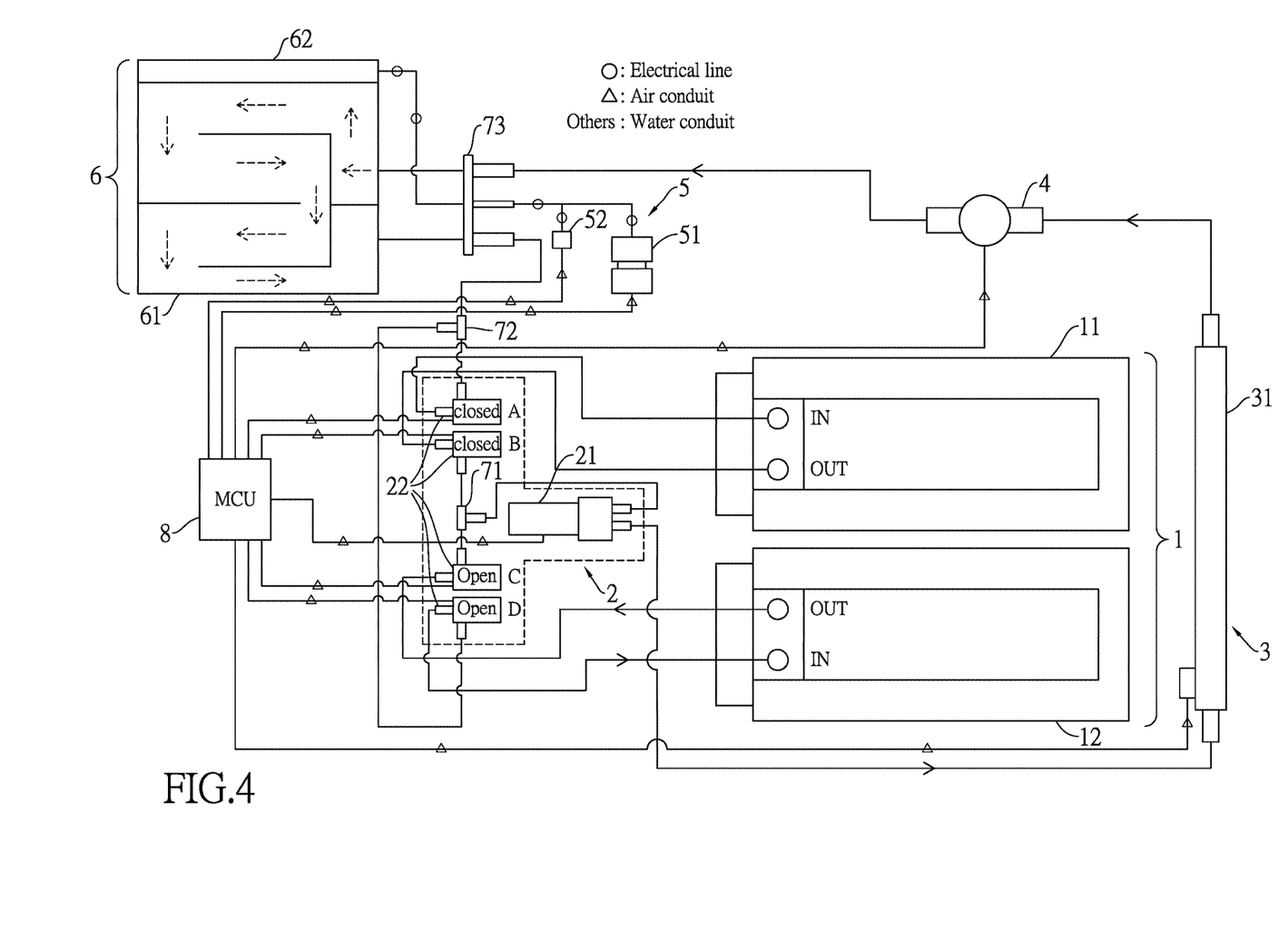
FIG. 4 is an operational schematic diagram showing the thermal therapy device in FIG. 2 under a hot water circulation mode.

With reference to FIG. 4, when the thermal therapy device is operated under the hot water circulation mode, the MCU 8 turns on the self-priming pump 21 and switches the two solenoid valves A and B to be closed and switches the two solenoid valves C and D to be open, water in the cold water container 12 is pumped by the self-priming pump 21 to sequentially circulate through the solenoid valve C, the first T tube 71, the self-priming pump 21, the water heater 31, the water temperature sensing unit 4, the water inlet of the three-way connector 73, the water bladder 61, the water outlet of the three-way connector 73, the second T tube 72, and the solenoid valve D, and returns to the cold water container 12. During the hot water circulation mode, the water heater 31 is turned on to heat water circulated through the water heater 31 when the temperature of the circulated water sensed by the water temperature sensing unit 4 is below the water temperature threshold, and the water heater 31 is turned off through the effect of the over-heat relay 32 when the temperature of the circulated water sensed by the water temperature sensing unit 4 reaches or exceeds the water temperature threshold. The heating effect of the circulated water in the water bladder 61 provides hot therapy treatment when the water bladder 61 is placed on a body portion to be treated.

Figure 5:
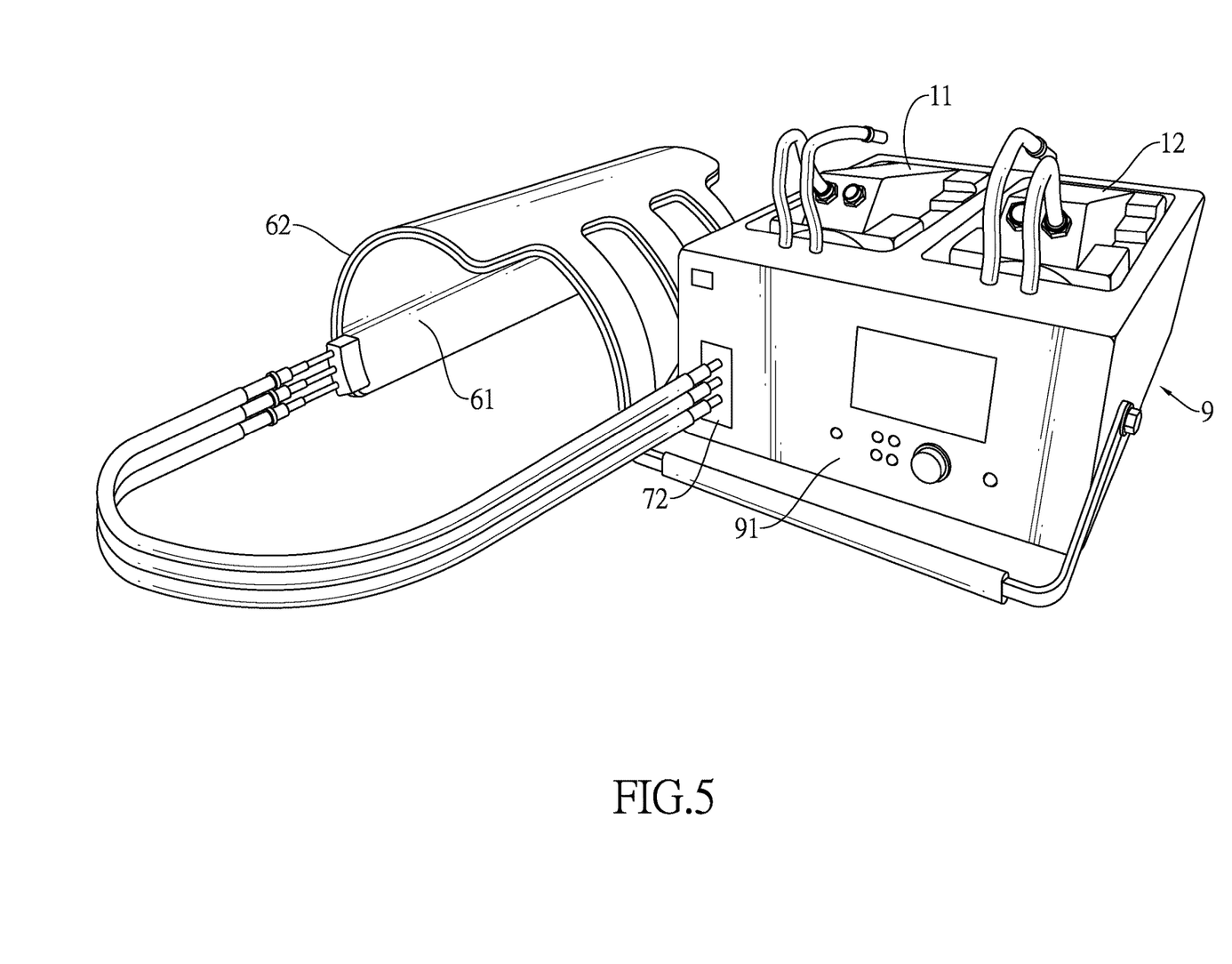
FIG. 5 is an operational perspective view of the thermal therapy device in FIG. 1 under a water return mode.
Figure 6:
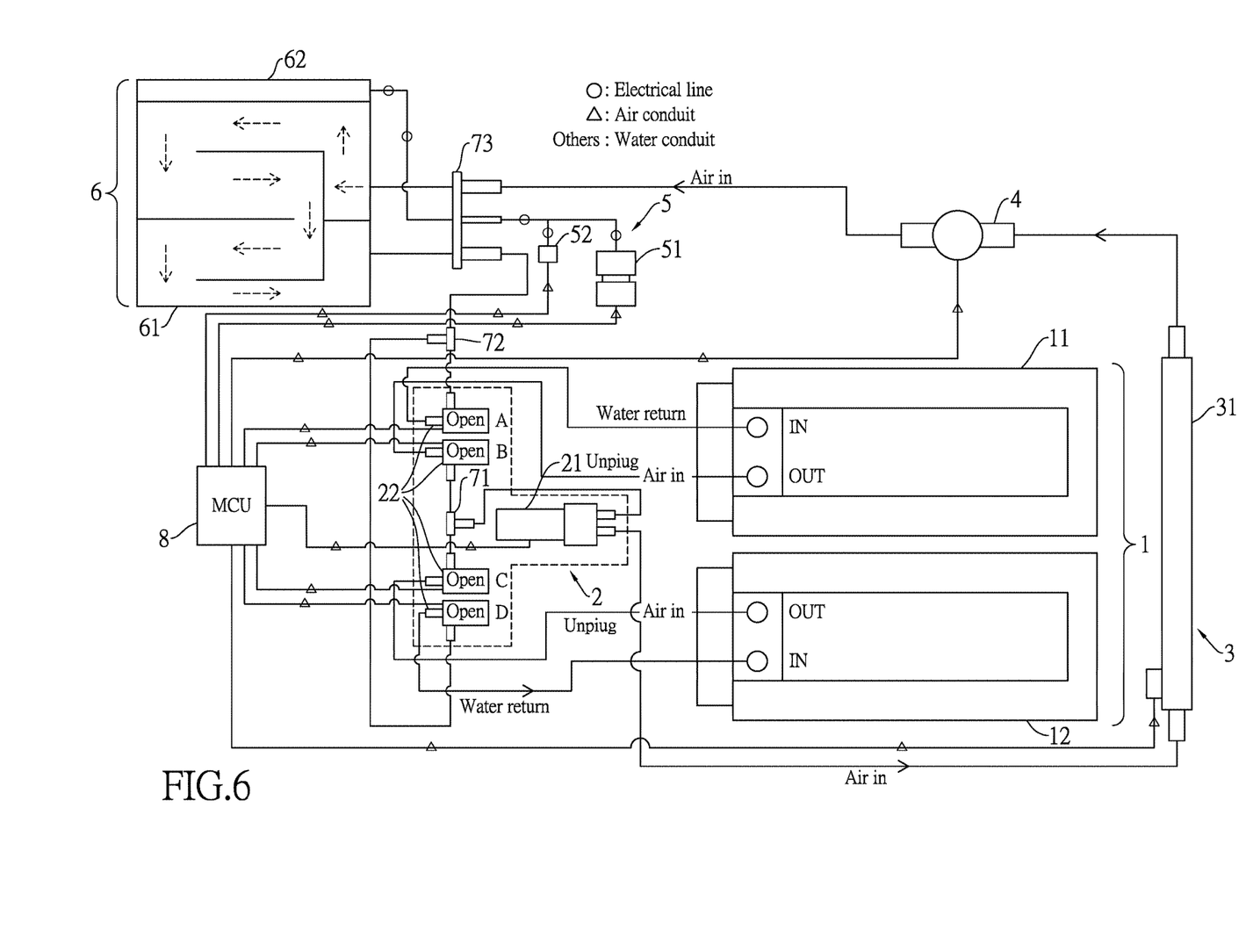
FIG. 6 is an operational schematic view of the thermal therapy device in FIG. 2 under a water return mode.

With reference to FIGS. 5 and 6, the thermal therapy device may be operated under a water return mode to evacuate water retained in the water bladder 61. Under the water return mode, the water conduits connected with the water outlets of the mixed ice and water container 11 and the cold water container 12 are manually unplugged from the outlet, the MCU 8 turns on the self-priming pump 21 and switches all the four solenoid valves A, B, C, D to be open, due to the effect of the self-priming pump 21, air is sucked in through the water conduits unplugged from the water outlet of the mixed ice and water container 11 and sequentially passes through the solenoid valve B, the first T tube 71, the self-priming pump 21, the water heater 31, the water temperature sensing unit 4, and the water inlet of the three-way connector 73 to enter the water bladder 61, and the water retained in the water bladder 61 is partially pushed by the air to sequentially flow through the water outlet of the three-way connector 73 and the second T tube 72 and returns to the mixed ice and water container 11 through the solenoid valve A and to the cold water container 12 through the solenoid valve D. Similarly, air sucked in through the water conduit unplugged from the water outlet of the cold water container 12 sequentially passes through the solenoid valve C, the first T tube 71, the self-priming pump 21, the water heater 31, the water temperature sensing unit 4, and the water inlet of the three-way connector 73 to enter the water bladder 61, and the water retained in the water bladder 61 is partially pushed by the air to sequentially flow through the water outlet of the three-way connector 73 and the second T tube 72 and returns to the mixed ice and water container 11 through the solenoid valve A and to the cold water container 12 through the solenoid valve D. Such water return mode may be continuously operated until all the water retained in the water bladder 61 goes to the mixed ice and water container 11 and the cold water container 12.

Figure 7:
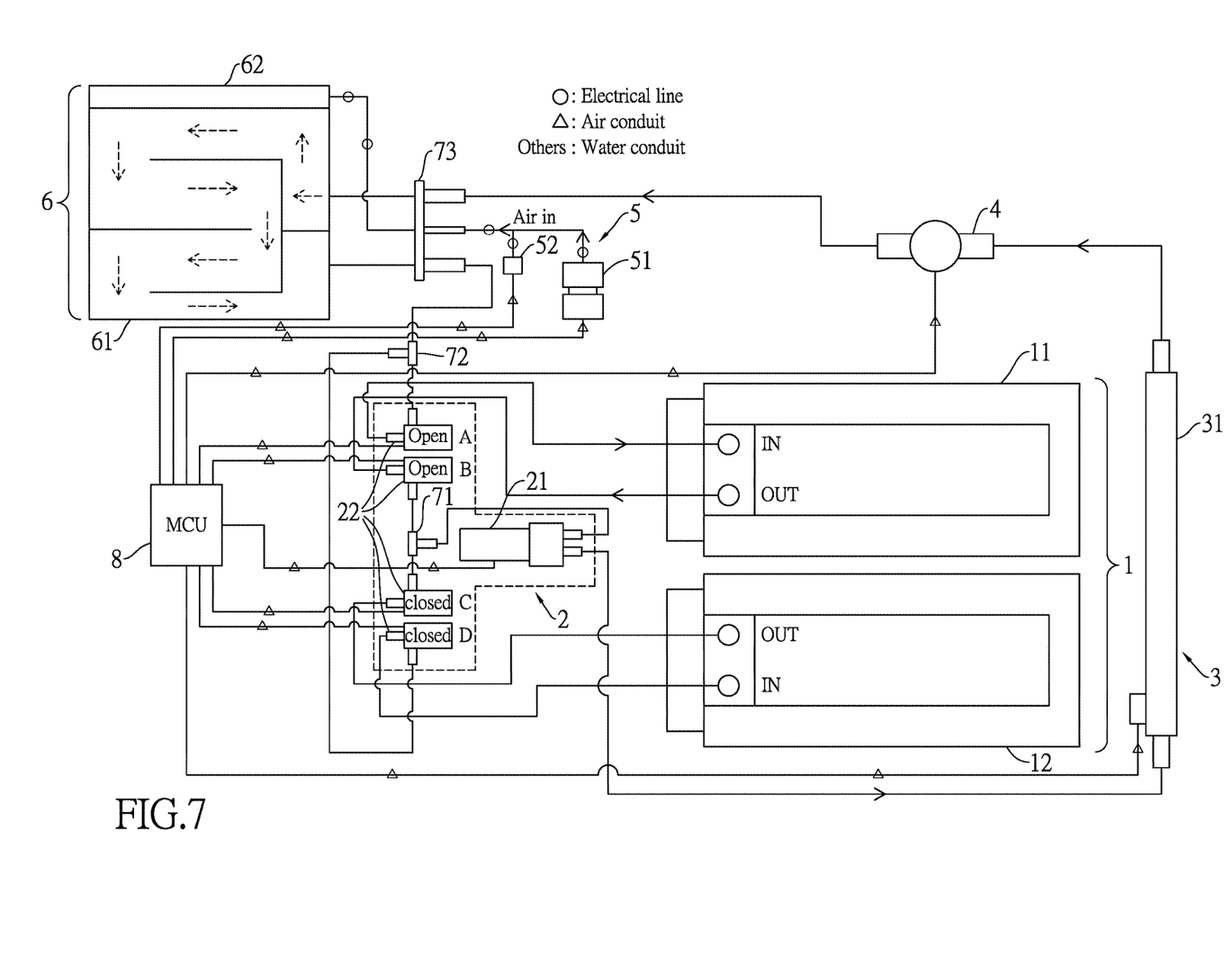
FIG. 7 is an operational schematic view of the thermal therapy device in FIG. 2 under an air pressure control mode.

As far as air supply to the air bladder 62 is concerned, with reference to FIG. 7, when the thermal therapy device is operated under the air pressure control mode and the air pressure sensed by the pressure sensor 52 is lower than the air pressure threshold, the MCU 8 turns on the pneumatic pump 51 to supply air to the air bladder 62 through the air passage of the three-way connector 73 to inflate the air bladder 62 until the air pressure sensed by the pressure sensor 52 reaches the air pressure threshold. Once the air pressure is greater than the air pressure threshold, the air bladder 62 is deflated until the air pressure is maintained at the air pressure threshold. Such air pressure control mode can be simultaneously performed with the cold water circulation mode or the hot water circulation mode.

As can be seen from the foregoing description, hot therapy treatment and cold therapy treatment can be both interchangeably provided through the thermal therapy device, such that the thermal therapy device in accordance with the present invention can provide comprehensive therapy treatments. Moreover, the air pressure control mode facilitates adjustment of holding pressure of the water bladder placed on the enclosure portion for treatment and improves the cold and hot therapy effects. Additionally, the water return mode helps evacuate water retained in the water bladder and return to the mixed ice and water container and the cold water container, thereby eliminating stinky odor and moss generation out of the retained water and ensuring more hygiene-keeping in use.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:
1. A thermal therapy device with interchangeable hot and cold water circulation and air pressure control, comprising:
  an enclosure having a control panel mounted thereon for configuring a water circulation mode, a water temperature threshold, an air pressure control mode, and an air pressure threshold;
  an ice and water containing unit having:
    a mixed ice and water container detachably mounted on the enclosure, filled with ice and water, providing chilled water to be circulated for cold therapy treatment, and having a water inlet and a water outlet; and
    a cold water container detachably mounted on the enclosure, filled with water to be circulated for hot therapy treatment, and having a water inlet and a water outlet;
  a water switching and circulation unit securely mounted inside the enclosure and having:
    a self-priming pump driving to circulate water or air entering therein; and
    a first solenoid valve, a second solenoid valve, a third solenoid valve and a fourth solenoid valve being normally closed, wherein the first solenoid valve is connected to the water inlet of the mixed ice and water container through a water conduit, the second solenoid valve is connected to the water outlet of the mixed ice and water container and the self-priming pump through water conduits, the third solenoid valve is connected to the water outlet of the cold water container and the self-priming pump through water conduits, and the fourth solenoid valve is connected to the water inlet of the cold water container through a water conduit;
  a water heating unit securely mounted inside the enclosure, connected with the self-priming pump through a water conduit, and heating water supplied from the self-priming pump;
  a water temperature sensing unit securely mounted inside the enclosure, connected with the water heating unit through a water conduit, and sensing temperature of water passing through the water temperature sensing unit;
  a therapy bladder assembly connected with the first solenoid valve and the fourth solenoid valve through water conduits, and having:
    a water bladder adapted to be placed on a body portion requiring a therapy treatment under the water circulation mode and having an inlet and an outlet; and
    an air bladder securely attached to a periphery of the water bladder;
  an air supply and pressure monitoring unit securely mounted inside the enclosure, connected to the air bladder, supplying air to the air bladder to put pressure on the water bladder under the air pressure control mode, and sensing an air temperature in the air bladder; and a microcontroller unit (MCU) securely mounted inside the control panel and electrically connected to the self-priming pump, the first solenoid valve, the second solenoid valve, the third solenoid valve, the fourth solenoid valve, the water heating unit, the water temperature sensing unit, and the air supply and pressure monitoring unit, wherein under the water circulation mode, the MCU is configured to turn on the self-priming pump, selectively switch a part of the first solenoid valve, the second solenoid valve, the third solenoid valve and the fourth solenoid valve to be open, and selectively turn on the water heating unit to continuously heat circulated water or turn off the water heating unit throughout the water circulation mode to maintain a water temperature of the circulated water sensed by the water temperature sensing unit at the water temperature threshold, and under the air pressure control mode, the MCU is configured to turn on the air supply and pressure monitoring unit to inflate or deflate the air bladder to maintain an air pressure of the air bladder sensed by the air supply and pressure monitoring unit at the air pressure threshold.

2. The thermal therapy device as claimed in claim 1, further comprising:
a water and air conduit connection unit having:
a first T tube having three ports respectively connected to the second solenoid valve, the third solenoid valve and the self-priming pump through water conduits;
a second T tube having three ports with two of the three ports respectively connected with the first solenoid valve and the fourth solenoid valve; and
a three-way connector having:
a water inlet connected between the inlet of the water bladder and the water temperature sensing unit through water conduits;
a water outlet connected between the outlet of the water bladder and a remaining port of the second T tube; and
an air passage allowing air connected to the air supply and pressure monitoring unit and the air bladder.

3. The thermal therapy device as claimed in claim 2, wherein the air supply and pressure monitoring unit has:
a pneumatic pump connected to the air passage of the three-way connector through an air conduit to supply air; and
a pressure sensor connected between the pneumatic pump and the three-way connector through another air conduit to sense the pressure of air pumped by the pneumatic pump.

4. The thermal therapy device as claimed in claim 3, wherein the water heating unit has:
a water heater mounted on a water conduit connected between an outlet of the self-priming pump and the water temperature sensing unit to heat water passing through the water conduit on which the water heater is mounted; and
an over-heat relay connected to the water heater to automatically switch off the water heater when water temperature sensed by the water temperature sensing unit is equal to or greater than the water temperature threshold.

5. The thermal therapy device as claimed in claim 4, wherein when the water circulation mode is a cold water circulation mode for cold therapy treatment, the MCU is configured to turn on the self-priming pump, switch the first solenoid valve and the second solenoid valve to be open, and switch the third solenoid valve and the fourth solenoid valve to be closed, such that water in the mixed ice and water container is pumped by the self-priming pump to sequentially circulate through the second solenoid valve, the first T tube, the self-priming pump, the water heater, the water temperature sensing unit, the water inlet of the three-way connector, the water bladder, the water outlet of the three-way connector, the second T tube, and the first solenoid valve and return to the mixed ice and water container, wherein during the cold water circulation mode, the MCU is configured not to turn on the water heater.

6. The thermal therapy device as claimed in claim 5, wherein when the water circulation mode is a hot water circulation mode for hot therapy treatment, the MCU is configured to turn on the self-priming pump, switch the first solenoid valve and the second solenoid valve to be closed, switch the third solenoid valve and the fourth solenoid valve to be open, such that water in the cold water container is pumped by the self-priming pump to sequentially circulate through the third solenoid valve, the first T tube, the self-priming pump, the water heater, the water temperature sensing unit, the water inlet of the three-way connector, the water bladder, the water outlet of the three-way connector, the second T tube, and the fourth solenoid valve and return to the cold water container, wherein during the hot water circulation mode, the MCU is configured to turn on the water heater to heat water circulated through the water heater when the temperature of the circulated water sensed by the water temperature sensing unit is below the water temperature threshold, and turn off the water heater through the effect of an overheat relay when the temperature of the circulated water sensed by the water temperature sensing unit reaches or exceeds the water temperature threshold.

7. The thermal therapy device as claimed in claim 6, wherein under the air pressure control mode, if the air pressure sensed by the pressure sensor is lower than the air pressure threshold, the MCU is configured to turn on the pneumatic pump to supply air to the air bladder through the air passage of the three-way connector to inflate the air bladder until the sensed air pressure reaches the air pressure threshold, wherein if the sensed air pressure is greater than the air pressure threshold, the MCU is configured to turn on the pneumatic pump to deflate the air bladder until the air pressure is maintained at the air pressure threshold, and wherein the air pressure control mode can be simultaneously performed with the cold water circulation mode or the hot water circulation mode.

8. The thermal therapy device as claimed in claim 7, wherein the control panel serves for further configuring a water return mode, wherein under the water return mode, the water conduits connected with the water outlets of the mixed ice and water container and the cold water container are configured to be manually unplugged from the outlet, the MCU is configured to turn on the self-priming pump and switches the first solenoid valve, the second solenoid valve, the third solenoid valve and the fourth solenoid valve to be open, such that air sucked in by the self-priming pump through the water conduits unplugged from the water outlet of the mixed ice and water container sequentially passes through the second solenoid valve, the first T tube, the self-priming pump, the water heater, the water temperature sensing unit, and the water inlet of the three-way connector to enter the water bladder, and water retained in the water bladder is partially pushed by the aft to sequentially circulate through the water outlet of the three-way connector and the second T tube and return to the mixed ice and water container through the first solenoid valve and to the cold water container through the fourth solenoid valve, and air sucked in by the self-priming pump through the water conduit unplugged from the water outlet of the cold water container sequentially passes through the third solenoid valve, the first T tube, the self-priming pump, the water heater, the water temperature sensing unit, and the water inlet of the three-way connector to enter the water bladder, and the water retained in the water bladder is partially pushed by the air to sequentially, circulate through the water outlet of the three-way connector and the second T tube and returns to the mixed ice and water container through the first solenoid valve and to the cold water container through the fourth solenoid valve.

9. The thermal therapy device as claimed in claim 6, wherein the control panel serves for further configuring a water return mode, wherein under the water return mode, the water conduits connected with the water outlets of the mixed ice and water container and the cold water container are configured to be manually unplugged from the outlet, the MCU is configured to turn on the self-priming pump and switch the first solenoid valve, the second solenoid valve, the third solenoid valve and the fourth solenoid valve to be open, such that air sucked in by the self-priming pump through the water conduits unplugged from the water outlet of the mixed ice and water container sequentially passes through the second solenoid valve, the first T tube, the self-priming pump, the water heater, the water temperature sensing unit, and the water inlet of the three-way connector to enter the water bladder, and water retained in the water bladder is partially pushed by the air to sequentially circulate through the water outlet of the three-way connector and the second T tube and return to the mixed ice and water container through the first solenoid valve and to the cold water container through the fourth solenoid valve, and air sucked in by the self-priming pump through the water conduit unplugged from the water outlet of the cold water container sequentially passes through the third solenoid valve, the first T tube, the self-priming pump, the water heater, the water temperature sensing unit, and the water inlet of the three-way connector to enter the water bladder, and the water retained in the water bladder is partially pushed by the air to sequentially circulate through the water outlet of the three-way connector and the second T tube and returns to the mixed ice and water container through the first solenoid valve and to the cold water container through the fourth solenoid valve.

10. The thermal therapy device as claimed in claim 5, wherein under the aft pressure control mode, if the aft pressure sensed by the pressure sensor is lower than the air pressure threshold, the MCU is configured to turn on the pneumatic pump to supply air to the air bladder through the aft passage of the three-way connector to inflate the air bladder until the sensed air pressure reaches the air pressure threshold, wherein if the sensed air pressure is greater than the air pressure threshold, the MCU is configured to turn on the pneumatic pump to deflate the air bladder until the air pressure is maintained at the air pressure threshold, and wherein the air pressure control mode can be simultaneously performed with the cold water circulation mode or the hot water circulation mode.

11. The thermal therapy device as claimed in claim 10, wherein the control panel serves for further configuring a water return mode, wherein under the water return mode, the water conduits connected with the water outlets of the mixed ice and water container and the cold water container are configured to be manually unplugged from the outlet, the MCU is configured to turn on the self-priming pump and switches the first solenoid valve, the second solenoid valve, the third solenoid valve and the fourth solenoid valve to be open, such that air sucked in by the self-priming pump through the water conduits unplugged from the water outlet of the mixed ice and water container sequentially passes through the second solenoid valve, the first T tube, the self-priming pump, the water heater, the water temperature sensing unit, and the water inlet of the three-way connector to enter the water bladder, and water retained in the water bladder is partially pushed by the air to sequentially circulate through the water outlet of the three-way connector and the second T tube and return to the mixed ice and water container through the first solenoid valve and to the cold water container through the fourth solenoid valve, and air sucked in by the self-priming pump through the water conduit unplugged from the water outlet of the cold water container sequentially passes through the third solenoid valve, the first T tube, the self-priming pump, the water heater, the water temperature sensing unit, and the water inlet of the three-way connector to enter the water bladder, and the water retained in the water bladder is partially pushed by the air to sequentially circulate through the water outlet of the three-way connector and the second T tube and returns to the mixed ice and water container through the first solenoid valve and to the cold water container through the fourth solenoid valve.

12. The thermal therapy device as claimed in claim 5, wherein the control panel serves for further configuring a water return mode, wherein under the water return mode, the water conduits connected with the water outlets of the mixed ice and water container and the cold water container are configured to be manually unplugged from the outlet, the MCU is configured to turn on the self-priming pump and switch the first solenoid valve, the second solenoid valve, the third solenoid valve and the fourth solenoid valve to be open, such that air sucked in by the self-priming pump through the water conduits unplugged from the water outlet of the mixed ice and water container sequentially, passes through the second solenoid valve, the first T tube, the self-priming pump, the water heater, the water temperature sensing unit, and the water inlet of the three-way connector to enter the water bladder, and water retained in the water bladder is partially pushed by the air to sequentially circulate through the water outlet of the three-way connector and the second T tube and return to the mixed ice and water container through the first solenoid valve and to the cold water container through the fourth solenoid valve, and air sucked in by the self-priming pump through the water conduit unplugged from the water outlet of the cold water container sequentially passes through the third solenoid valve, the first T tube, the self-priming pump, the water heater, the water temperature sensing unit, and the water inlet of the three-way connector to enter the water bladder, and the water retained in the water bladder is partially pushed by the air to sequentially circulate through the water outlet of the three-way connector and the second T tube and returns to the mixed ice and water container through the first solenoid valve and to the cold water container through the fourth solenoid valve.

* * * * *